(12) United States Patent
Goldspink

(10) Patent No.: US 6,221,842 B1
(45) Date of Patent: Apr. 24, 2001

(54) METHOD OF TREATING MUSCULAR DISORDERS

(75) Inventor: Geoffrey Goldspink, London (GB)

(73) Assignee: University College London, London (GB)

( * ) Notice: Subject to any disclaimer, the term of this patent is extended or adjusted under 35 U.S.C. 154(b) by 0 days.

(21) Appl. No.: 09/142,583

(22) PCT Filed: Mar. 11, 1997

(86) PCT No.: PCT/GB97/00658

§ 371 Date: Oct. 29, 1998

§ 102(e) Date: Oct. 29, 1998

(87) PCT Pub. No.: WO97/33997

PCT Pub. Date: Sep. 18, 1997

(30) Foreign Application Priority Data

Mar. 11, 1996 (GB) .................................................. 9605124

(51) Int. Cl.$^7$ ............................. A61K 38/30; C07K 14/65
(52) U.S. Cl. .................. 514/12; 514/21; 530/399
(58) Field of Search .................... 514/3, 12, 13, 514/21; 530/303, 324, 325, 350, 399

(56) References Cited

FOREIGN PATENT DOCUMENTS

| 0 229 750 | 7/1987 | (EP) . |
| WO 92/11865 | 7/1992 | (WO) . |
| WO 93/0923 | 5/1993 | (WO) . |
| WO 95/13290 | 5/1995 | (WO) . |

OTHER PUBLICATIONS

Chew et al, Endocrinology vol. 136, No. 5 (1995) pp 1939–1944 An Alternatively Spliced Human etc.
Yang et al J. of Muscle Research and Cell Motility 17, 487–495 (1996) Cloning and Characterization etc.
Goldspink et al Amer.J. of Physiology (Feb. 1995)p. vol. 268, No. 2 Muscle Growth in response to mechanical stimuli.
Edwall et al Endocrinology, vol. 124, No. 2 (1989) p. 820–825 Induction of Insulin–Like Growth Factor etc.
DeVol et al Amer. J. of Physiology(Jul. 1990)vol. 259, No. 1 E89–E95 Activation of insulin–like growth factor etc.
Lowe et al Molecular Endocrinology vol. 2, No. 6,(Jun. 1988) 528–535 Distribution and Regulation of Rat Insulin etc.
Han et al Science, vol. 236, 1(Apr. 1987)Cellular Localization of Somatomedin (Insulin–Like Growth Factor) etc.
Jansen et al Nature 306, 609–611, (1983)Sequence of cDNA encoding human insulin–like growth factor I etc.
Caroni et al J. of Neuroscience,(May 1994)14(5): 3378–3388 Signalling by Insulin–Like Growth Factors in
Goldspink et al Amer J. of Physiology 262, R356–R363, (1992)Gene expression in skeletal muscle in etc.

(List continued on next page.)

Primary Examiner—Jeffrey E. Russel
(74) Attorney, Agent, or Firm—Nixon & Vanderhye P.C.

(57) ABSTRACT

The invention provides pharmaceutical compositions comprising particular isoforms of human insulin-like growth factor I (IGF-I). An isofoim of the invention is an IGF-I polypeptide corresponding to the mechanical-stimulation-specific, stretch-inducible IGF-I isoform present in stretched rabbit EDL muscle, the polypeptide comprising peptides encoded by IGF-I exons 4, 5 and 6 when transcribed in the reading frame of the stretched rabbit EDL muscle isoform and the polypeptide having the ability to induce growth of muscle tissue. The isoforms of the invention have utility in treating muscular disorders, especially muscular dystrophy. Methods of treatment of such muscular disorders in humans and animals with the isoforms of the invention are also provided.

10 Claims, 5 Drawing Sheets

```
Tyr Gln Pro Pro Ser Thr Asn Lys Lys  MET  Lys Ser Gln Arg Arg Arg Lys
Tyr Gln Pro Pro Ser Thr Asn Lys Asn  Thr  Lys Ser Gln Arg Arg Lys
Ser Gln Pro Leu Ser Thr His Lys Lys  Arg  Lys Leu Gln Arg Arg Arg Lys
```

OTHER PUBLICATIONS

Goldspink et al European J. of Physiology(1986)407:333–340 The effect of hypokinesia and hypodynamia etc.

Valenzuela et al Neuron, vol. 15, 573–584 (Sep. 1995)Receptor Tyrosine Kinase Specific for the Skeletal etc.

Goldspink et al J. Physiology(1996), 162P–163P, Local Growth Regulation is Associated with an Isoform etc.

Fig.3.

```
TTGCTCACCTTTACCAGCTCGGCCACAGCCGGACCGGAGACGCTCTGCGGTGCTGAGCTG    60
LeuLeuThrPheThrSerSerAlaThrAlaGlyProGluThrLeuCysGlyAlaGluLeu
                         B-->

GTGGATGCTCTTCAGTTCGTGTGTGGAGACAGGGGCTTTTATTTCAACAAGCCCACAGGA   120
ValAspAlaLeuGlnPheValCysGlyAspArgGlyPheTyrPheAsnLysProThrGly
                                                          C->

TACGGCTCCAGCAGTCGGAGGGCACCTCAGACAGGCATCGTGGATGAGTGCTGCTTCCGG   180
TyrGlySerSerSerArgArgAlaProGlnThrGlyIleValAspGluCysCysPheArg
                         A-->

AGCTGTGATCTGAGGAGGCTGGAGATGTACTGTGCACCCCTCAAGCCGGCAAAGGCAGCC   240
SerCysAspLeuArgArgLeuGluMETTyrCysAlaProLeuLysProAlaLysAlaAla
                                                D-->

288
CGCTCCGTCCGTGCCCAGCGCCACACCGACATGCCCAAGACTCAGAAGTATCAGCCTCCA   300
ArgSerValArgAlaGlnArgHisThrAspMETProLysThrGlnLysTyrGlnProPro
E-->                                                 Eb-->
                               340
TCTACCAACAAGAAAATGAAGTCTCAGAGGAGAAGGAAAGGAAGTACATTTGAAGAACAC   360
SerThrAsnLysLysMETLysSerGlnArgArgArgLysGlySerThrPheGluGluHis
                                            GluValHisLeuLysAsnTh
         Ea-->                                ◆ ◆

AAGTAGAGGGAGTGCAGGAAACAAGAACTACAGGATGTAGGAAGACCCTTCTGAGGAGTG   420
Lysend
rSerArgGlySerAlaGlyAsnLysAsnTyrArgMETend
  ◆

AAGAAGGACAGGCCACCGCAGGACCCTTTGCTCTGCACAGTTACCTGTAAACATTGGAAT   480
ACCGGCCAAAAAATAAGTTTGATCACATTTCAAAGATGGCATTTCCCCCAATGAAATACA   560
CAAGTAAACATTC
```

Fig.4.

| Tyr | Gln | Pro | Pro | Ser | Thr | Asn | Lys | Lys | MET | Lys | Ser | Gln | Arg | Arg | Arg | Lys |
| Tyr | Gln | Pro | Pro | Ser | Thr | Asn | Lys | Asn | Thr | Lys | Ser | Gln | Arg | Arg | | Lys |
| Ser | Gln | Pro | Leu | Ser | Thr | His | Lys | Lys | Arg | Lys | Leu | Gln | Arg | Arg | Arg | Lys |

Fig.5.

HUMAN IGF-I Ea isoform

SIGNATURE

```
Pst-I                                                            50
5'-CTGCAGGGGGGGGGGGGGGGGGGGCTTCA GAA GCA ATG GGA AAA ATC AGC AGT
                               Ser Glu Ala Met Gly Lys Ile Ser Ser
                               -50
                                                                100
CTT CCA ACC CAA TTA TTT AAG TGC TGC TTT TGT GAT TTC TTG AAG GTG
Leu Pro Thr Gln Leu Phe Lys Cys Cys Phe Cys Asp Phe Leu Lys Val
        -40                                     -30

AAG ATG CAC ACC ATG TCC TCC TCG CAT CTC TTC TAC CTG GCG CTG TGC
Lys Met His Thr Met Ser Ser Ser His Leu Phe Tyr Leu Ala Leu Cys
                         -20

150
CTG CTC ACC TCC ACC AGC TCT GCC ACG GCT GGA CCG GAG ACG CTC TGC
Leu Leu Thr Ser Thr Ser Ser Ala Thr Ala Gly Pro Glu Thr Leu Cys
-10                                       -1  1

200
GGG GCT GAG CTG GTG GAT GCT CTT CAG TTC GTG TGT GGA GAC AGG GGC
Gly Ala Glu Leu Val Asp Ala Leu Gln Phe Val Cys Gly Asp Arg Gly
                 10                                       20

250
TTT TAT TTC AAC AAG CCC ACA GGG TAT GGC TCC AGC AGT CGG AGG GCG
Phe Tyr Phe Asn Lys Pro Thr Gly Tyr Gly Ser Ser Ser Arg Arg Ala
                     30

300
CCT CAG ACA GGT ATC GTG GAT GAG TGC TGC TTC CGG AGC TGT GAT CTA
Pro Gln Thr Gly Ile Val Asp Glu Cys Cys Phe Arg Ser Cys Asp Leu
  40                                           50
```

Fig.5 (Cont).

```
           350
AGG AGG CTG GAG ATG TAT TGC GCA CCC CTC AAG CCT GCC AAG TCA GCT
Arg Arg Leu Glu Met Tyr Cys Ala Pro Leu Lys Pro Ala Lys Ser Ala
                         60                              70

400
CGC TCT GTC CGT GCC CAG CGC CAC ACC GAC ATG CCC AAG ACC CAG AAG
Arg Ser Val Arg Ala Gln Arg His Thr Asp Met Pro Lys Thr Gln Lys
                                     80

450
GAA GTA CAT TTG AAG AAC GCA AGT AGA GGG AGT GCA GGA AAC AAG AAC
Glu Val His Leu Lys Asn Ala Ser Arg Gly Ser Ala Gly Asn Lys Asn
                 90                                  100

500
TAC AGG ATG TAG GAAGACCCTCCTGAGGAGTGAAGAGTGACATGCCACC
Tyr Arg Met ***

550
GCAGGATCCTTTGCTCTGCACGAGTTACCTGTTAAACTTTGGAACACCTACCAAAAAATA 600                                               650
AGTTTGATAACATTTAAAAGATGGGCGTTTCCCCCAATGAAATACACAAGTAAACATTCC

700
AACATTGTCTTTAGGAGTGATTTGCACCTTGCAAAAATGGTCCTGGAGTTGGTAGATTGC

750
TGTTGATCTTTTATCAATAATGTTCTATAGAAAAGAAAAAAAAACCCCCCCCCCCCCCT

GCAGT-3'
Pst-I
```

METHOD OF TREATING MUSCULAR DISORDERS

FIELD OF THE INVENTION

The present invention relates to improvements in treating muscle disorders and related conditions using insulin-like growth factor I.

BACKGROUND OF THE INVENTION insulin-like growth factor I (IGF-I) is a peptide present in the plasma and other body fluids. In its mature processed form it comprises 70 amino acids and can stimulate growth of a wide range of cell types. Human IGF-I have been cloned and its cDNA sequence can be found in Jansen et al, Nature, 1993 (reference 11 below). The cDNA sequence encodes a precursor (also known as the D-chain), a mature 70 amino acid comprising the B, C and A regions respectively, and a C-terminal region which is termed the E-peptide. Recently, it has been found that the E-peptide can exist in different isoforms. This arises as a result of alternative splicing at the mRNA level. Chew et al report the existence of three alternatively spliced T-terminal regions of human IGF-I. One of the isoforms produced is as a result of splicing between exons 4, 5 and 6 of the gene and this predicts a prepro-IGF-I molecule of 158 amino acids including a C-terminal peptide, the Ec peptide of 24 amino acids in length. This Ec peptide appears to correspond to the Eb peptide found in rat IGF-I.

IGF-I has been proposed for use of a number of disorders relating to muscle atrophy and related conditions. For example, WO92/11865 proposes the use of human IGF-I for the prevention or treatment of cardiac disorders and for the promotion of cardiac muscle protein synthesis, for prevention or treatment of cardiomyophthies, acute heart failure or acute insult including myocarditis or myocardial infarction and for improving cardiac output by increasing heart/volume. WO95/13290 relates to the use of IGF-I for treating muscular disorders such as muscular dystrophy and related progressive skeletal muscle weakness and wasting.

WO93/09236 teaches methods of gene therapy using myogenic vector systems comprising promoters suitable for use in muscle cells. Such vectors may be introduced into a human patient for the treatment of muscle atrophy in ageing humans, muscle atrophy induced by spinal cord injuries or neuromuscular diseases.

A difficulty with the use of IGF-I is that this peptide is responsible for a wide range of effects within the human body. Although IGF-I is produced in muscle cells it is also produced in the liver from where it circulates and is involved in regulating metabolism. Administration of IGF-I may thus induce side-effects including hypoglycaemia.

De Vol et al (1990), Am. J. Physiol. 259, E89–E95) report that IGF-I expression is elevated during work-induced skeletal muscle growth.

SUMMARY OF THE INVENTION

We have investigated the production of IGF-I in skeletal muscles and have surprisingly found that whereas resting muscles normally produce the liver IGF-I isoform including the Ea peptide, muscle cells induced to undergo rapid hypertrophy using active stretch rapidly up-regulate the production of a different IGF-I isoform. We have thus found that the IGF-I Ec isoform in humans, corresponding to the IGF-I Eb isoform in rats and rabbits, may play an important role in targeting the action of IGF-I to muscle cells. Thus, treatment of muscular disorders such as those mentioned above may be improved by the use of the human Ec isoform or the Ec peptide of human IGF-I.

Accordingly, the present invention provides a human IGF-I polypeptide or functional derivative thereof characterised by the presence of the Ec peptide for use in a method of treatment or therapy of the human or animal body. The invention also provides pharmaceutical compositions comprising such polypeptides.

The invention further provides a method for the treatment of muscular disorders of the human body which comprises administering to a patient in need of such treatment an effective amount of IGF-I or a functional derivative thereof which is characterised by the presence of Ec peptide.

BRIEF DESCRIPTION OF THE DRAWINGS

FIG. 3. DNA (SEQ ID NO: 3, 5) and derived amino acid (SEQ ID NO: 4, 6). DNA (SEQ ID NO: 3) and derived amino acid (SEQ ID NO: 4) sequences of rabbit IGF-1 cDNA isolated from stretched muscle: the two types of cDNA sequence differ by the presence (IGF-1Eb) or absence (IGF-IEa) of a 52 base pair insert (underline) from position 288 through position 340. The insert altered the derived C-terminal amino acid sequence of the E peptide (underline in IGF-1Eb case), changed the reading frames and used two different TAG stop codons (end). The putative glycosylation site (Asn-Thr-Ser) (marked by ♦♦♦) is present in the Ea but not in the Eb peptide. The DNA sequences of SEQ ID NOs: 3 and 5 are the same. The amino acid sequence of SEQ ID NO: 4 reflects the presence of the 52 base pair insert in the cDNA. The amino acid sequence of SEQ ID NO: 6 give the alternative C-terminus in the absence of the 52 base pair insert.

FIG. 4. Alignment of the three derived amino acid sequences of the inserts from rat liver (bottom) (SEQ ID NO: 9), human liver (middle) (SEQ ID NO: 8) and rabbit stretched muscle (top) (SEQ ID NO: 7). Identical amino residues are shown by the boxes.

FIG. 5. DNA (SEQ ID NO: 10) and encoded amino acid (SEQ ID NO: 11) sequence of the human IGF-1 Ea isoform within a Pst-I fragment.

Figure 1:
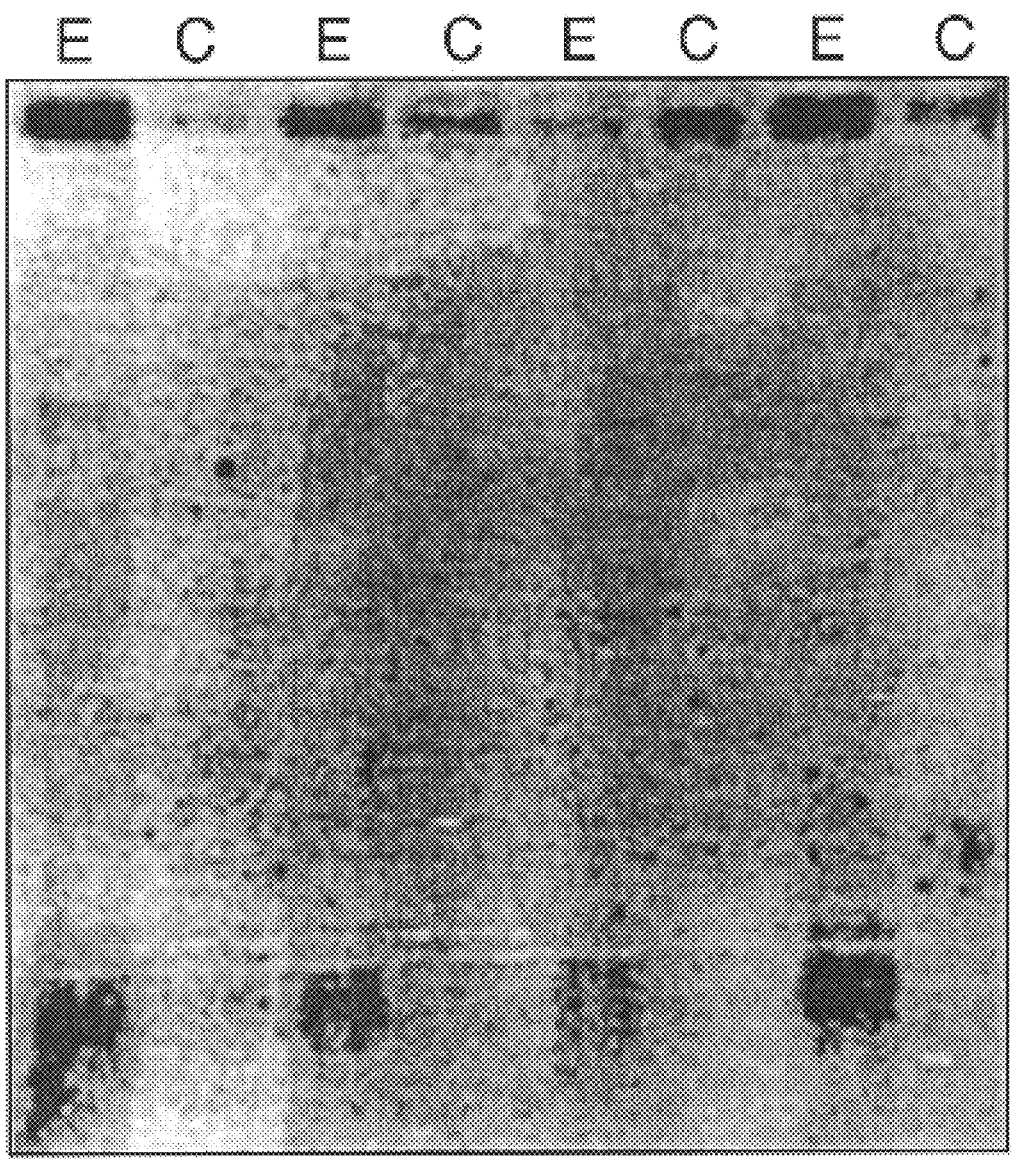
FIG. 1. Expression of IGF-I mRNA studied by Northern blotting in stretched (E) and control (C) extensor digitorum longus (EDL) muscle.
Figure 2A:
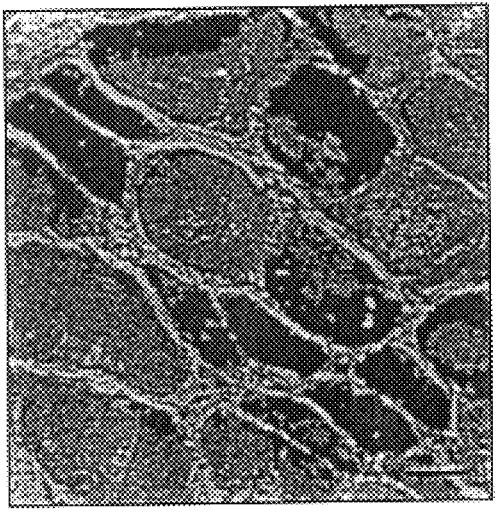
FIG. 2. Localisation and distribution of IGF-I mRNA in stretched (A, transverse section; B, longitudinal section) and control (C) extensor digitorum longus (EDL) muscle. The sense RNA probe from the same clone was used on the stretched muscle (D) as a negative control. Scale bar, 30 $\mu$m.
Figure 2B:
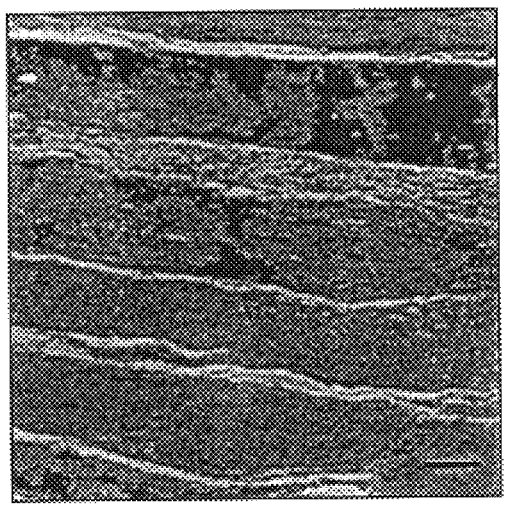
Figure 2C:
Figure 2D:
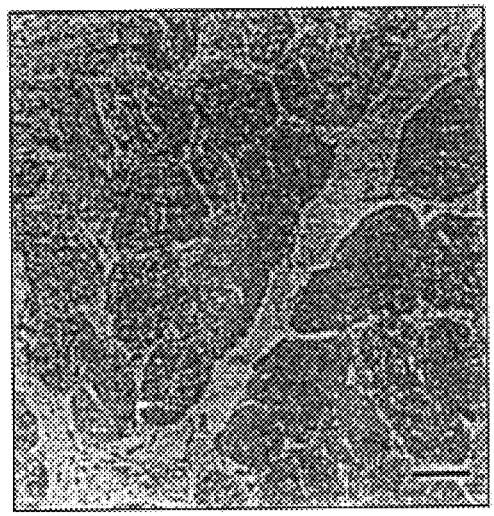

The IGF-I isoform to which the invention relates may thus be used in methods of treating disorders relating to muscle atrophy and related conditions. This includes the use of human IGF-I for the prevention or cardiac disorders, diseases where promotion of cardiac muscle protein synthesis is a beneficial treatment, cardiomyophthies, acute heart failure or acute insult including myocarditis or myocardial infarction. The IGF isoform may also be used for improving cardiac output by increasing heart/volume.

Other muscular disorders which may be treated include muscular dystrophy, e.g. Duchenne or Becker muscular dystrophy, as well as autosomal dystrophies, and related progressive skeletal muscle weakness and wasting. The treatment of muscle atrophy in ageing humans, muscle atrophy induced by spinal cord injuries or neuromuscular diseases may also be treated by the present invention.

Therapy with the appropriate IGF-I may also promote healing of bone fractures and maintenance of bone in old age.

Pharmaceutically acceptable carriers or diluents include those used in formulations suitable for oral or parenteral (e.g. intramuscular or intravenous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

The polypeptide of the invention may be administered by any suitable route, for example orally or injection, e.g. subcutaneous, intramuscular or intravenous injection, or alternatively may be produced in situ in a patient as a result of gene therapy treatment, for example as disclosed in WO93/09236, the contents of which are incorporated herein by reference.

WO95/13290, the contents of which are incorporated herein by reference, describes dose ranges of recombinant human IGF-I (the mature 70 amino acid polypeptide) in the range of 0.06 to 0.12 mg/kg per dose and IGF-I polypeptides comprising the Ec peptide may also be administered at this dose range. Doses may be administered at daily intervals or less frequently, for example at twice weekly or weekly intervals.

The IGF-I will preferably be a polypeptide comprising the 70 amino acid sequence of mature human IGF-I together with the Ec region which in humans corresponds to the Eb region of rabbit IGF-I set out in FIG. 3 of the accompanying Example.

The human Ec region is set out in FIG. 4. FIG. 5 shows the entire human cDNA sequence encoding the human Ea isoform.

While not wishing to be bound by any one particular theory we believe the human Ec isoform may be responsible for its activity via action on a receptor different from the normal IGF-I receptor. The presence of Ec region is believed to be responsible for binding to this receptor and thus derivatives of IGF-I Ec which retain the ability to induce the growth of muscle tissue may be used. Such derivatives may include further N-terminal truncations of the mature 70 amino acid sequence. This may be tested by bridging methods known as such to those of skill in the art, for example, by administration of such polypeptides (or mammalian equivalents thereof) to a mammal such as a rabbit or rat and observing the amount of muscle growth.

IGF-I Ec may be produced by any suitable means. Usually, this will be by recombinant means. For example, mRNA encoding the Ec isoform may be amplified using PCR primers as described in the accompanying Examples and the amplified product inserted into a suitable expression vector. IGF-I is produced by recombinant means commercially and these commercial methods may be used to produce the IGF-I Ec isoform. The vector may be any suitable recombinant vector known in the art for recombinant proteins. The vector will contain control signals for the expression of the IGF-I Ec protein operably linked to an open ring frame encoding said protein. The promoter will be compatible with a suitable host cell, for example a bacterial, yeast, insect or mammalian cell.

The following Example illustrates the invention. Insulin-like growth factor 1 (IGF-1) is a 70-residue polypeptide with important functions in the regulation of somatic growth, development and differentiation. The liver is a primary target for pituitary growth hormone (GH) which is stimulated to synthesize IGF-1. The resultant increase in circulating level of IGF-1 promotes cell division and is a major factor in regulating the growth of the body as a whole. In several tissues there is also apparently a local system of growth regulation e.g. skeletal muscle which is able to undergo rapid hypertrophy to adapt to overload. It was, therefore, important to investigate the role of IGF-1 in the locally regulated growth response.

Information on the organization of the IGF-1 gene is now available for several species, among which the human and rat genes are most extensively studied [1–5]. The structure of the IGF-1 gene is well conserved among mammals and contains several notable features, including an unexpectedly large size and the presence of alternatively spliced exons. In humans the IGF-1 gene comprises at least six exons (designated exon 1, 2, 3, 4, 5 and 6) spanning a region of over 90 kilobases (kb) of genomic, DNA. Exons 1 and 2 are alternative leader exons [4,5] with distinct transcription start sites which are differentially spliced to the common exon 3 and produce class 1 and class 2 IGF-1 mRNA transcripts respectively [6–8]. Exons 3 and 4 code for the mature IGF-1 peptide (B, C, A and D domains) as well as the first 16 amino acid of the E Domain. Exons 5 and 6 each encodes an alternative part of a distinct extension peptide, named the E domain. This is followed by the termination codons of precursor IGF-1, 3' untranslated regions and poly(A) addition signal sites [2]. Sequence analyses of IGF-1 peptide purified from human plasma demonstrated that mature IGF-1 contains A, B, C and D domains. The A and B domains are homologous to the A and B chains of insulin [9].

Analysis of liver IGF-1 cDNA sequences also demonstrated the presence of an E peptide domain which was an extension of the D peptide domain [10–12]. A later study using antibodies directed against the E peptide of human IGF-1 confirmed that the mRNA sequence encoding the E peptide is actively translated and suggested that the E peptide circulates as part of the IGF-1 prohormone [13]. In rat liver IGF-1 mRNAs code for a 35-amino-acid E peptide sequence (IGF-1Ea). However an isoform (IGF-1Eb) with a different 41-amino-acid Eb domain has been detected at very low levels [14]. These two mRNAs encode alternative E peptide due to the presence (IGF-1Eb) or absence (IGF-1Ea) of a 52 base insert in the region coding the E domain [10, 14]. In human there are also IGF-1 cDNAs encoding three different Ea, Eb and Ec domains. The Ea and Eb-type cDNAs contain entirely different 3' sequences which specify different 3' untranslated sequences as well as different E domain coding sequences [2]. This is due to splicing in 3' exons [2]. The Ec is a exon 4-5-6 spliced cDNA which predicts a precursor IGF-1 of 158 amino-acid residues and is the human counterpart of the rat Eb [15]. The physiological role of the alternative E peptide generated from IGF-1Ea, IGF-1Eb and IGF-1Ec remains unknown.

Skeletal muscle has been shown to increase in mass very rapidly in response to passive stretch. The mature rabbit anterior tibialis is able to increase in mass by 35% in 4 days in this way [16]. From previous work [17, 18] this was known to be associated with the rapid production of new sarcomeres which are added serially at the ends of the fibre to existing myofibrils. Muscle stretch has been shown to result in an increase of IGF-1 mRNA as measured by RT-PCR [19]. However it is not know whether the IGF-1 gene is expressed by the muscle fibres themselves or by satellite cells or what isoforms of IGF-1 are involved. The regulation of muscle growth in vivo remains poorly understood, although the original observations on compensatory muscle hypertrophy implied that a component of muscle growth regulation is a localized, self-contained, and selflimiting process.

Against this background, the current study was designed to determine whether local induction of muscle growth in vivo may involve alternative IGF-1 gene expression with different mRNA splicing for IGF-1 and localized fibre type expression.

MATERIALS AND METHODS

1. Animals and Muscle Stretch Procedure: New Zealand white rabbits were used. The extensor digitorum. longus (EDL) muscle was subjected to acute stretch by immobilizing the left hind limb in, the extended position using a plaster cast. As was previously reported this results in a 35% increase in muscle mass within a few days [16]. After 6 days, euthanasia was induced by intravenous injection of an over dose of sodium pentobarbitone into the marginal ear vein. The EDL was immediately dissected out from both hind legs. The right hind leg served as the control. Each muscle was cut transversely into 2 parts, one part was fixed in freshly prepared 4% paraformaldehyde fixative at 4° C. for 2 hours and later processed and embedded in paraffin wax. The second part was packed into a 1.5 ml tube and directly frozen in liquid nitrogen and stored at −70° C. to await total RNA isolation.

2. RNA isolation: Total cellular RNA was isolated from stretched and normal muscle using the single-step method with acid guanidinium thiocyanate-phenol-chloroform extraction [20].

3. Synthesis of probes for Northern blot and in situ hybridisation: The oligonucleotide 5' TTGGGCATGT-CAGTGTGG 3' (SEQ ID NO: 1) which is complementary to the sequence of exon 4 of the IGF-1 gene was used as primer to synthesise cDNA of the IGF-1 mRNA by reverse transcriptase (RAV-2, Amersham). The cDNA was then amplified by PCR using two oligonucleotide primers (5' GCT-TGCTCACCTTTACCAGC 3' (SEQ ID NO: 2) and 5' TTGGGCATGTCAGTGTGG 3' (SEQ ID NO: 1). A 280 base pair PCR product covering exon 3 and part of exon 4 of the IGF-1 gene was subcloned into pBS+ phagemid vector (Stratagene) including T3 and T7 promoters. Labelled sense and antisense RNA probes were synthesized by in vitro transcription with RNA polymerase using digoxigen in labelled uridine-triphosphate as substrate (Boehringer Mannheim) according to the manufacturers instructions. These probes were used for both Northern blotting and in situ hybridization.

4. Northern blotting: Samples containing the same amount (20 μg) of total RNA were subjected to Northern blotting. The 280 bp antisense probe described above was used. Prehybridization (1 hour) and hybridization (15 hours) were carried out at 6° C. in hybridization buffer [50% formamide; 5×SSC; 2% blocking reagent; 0.1% N-lauroylsarcosine; 0.02% SDS]. Washing was carried out at high stringency 2×5 minutes at room temperature with 1×SSC and 0.1% SDS, 2×15 minutes at 68° C. with 0.1× SSC and 0.1% SDS. The hybridized probe was detected by chemiluminescence according to the manufacturers instructions (Boehringer Mannheim). The blot filter was exposed to X-ray film for 6 hours.

5. In situ hybridization: The muscle tissues were cut in 10 μm sections. Both transverse and longitudinal sections were taken and mounted onto autoclaved slides coated with 2% 3aminopropyltriethoxy-silane (Sigma). The sections were dewaxed by washing in xylene 3 times for 2 minutes each and rehydrated in a series of methanol solutions. The sections were then denatured by incubating in 0.2 N HCl at room temperature for 20 minutes, heated in 2×SSC at 70° C. for 20 minutes and digested with pronase (10 μg/ml, Boehringer Mannheim) in 5 mM Tris.HCl for 15 minutes and was finally placed in 0.1 M triethanolamine (TEA) buffer, to which acetic anhydride was added to a final concentration of 0.5% and incubated for 10 minutes in order to block polar and charged groups in the sections. Hybridization was carried out in hybridization buffer [50% deionised formamide; 5×SSC; 5×Denhardts solution; 250 μg/ml yeast t-RNA; 250 μg/ml denatured salmon sperm DNA; 4 mM ethylenediaminetetraacetic acid (EDTA)] containing the DIG-labelled antisense or sense RNA probe consisting of the 280 bp sequence derived from exons 3 and part of exon 4 of the IGF-1 gene. The final concentration of probe was 1000 ng/ml. The hybridization was carried out at 68° C. for 1 hour and then allowed to cool down to 42° C. at which it was kept overnight in a humid chamber. After hybridization the sections were incubated with RNase A (100 μg/ml, Sigma) to remove the unbound single strand RNA probe. Washing was carried out at high stringency, 25 minutes in 2×SSC at room temperature, 15 minutes in 1×SSC at room temperature, 30 minutes in 0.5×SSC at 42° C. and 30 minutes in 0.5×SSC at room temperature. The hybridized probe was detected by anti-digoxigenin-AP antibody conjugate, Fab fragments (1.5 U/ml, Boehringer Mannheim), according to manufacturers instructions.

6. Synthesis and molecular cloning of muscle IGF-1 cDNA: The first strand cDNA was synthesized by reverse transcriptase (RAV-2, Amersham.) from muscle total RNA with oligo dT primers and then amplified by the 3' rapid amplification of cDNA ends polymerase chain reaction (3' RACEPCR) with an IGF-1 gene specific primer (5' GCT-TGCTCACCTTTACCAGC 3' (SEQ ID NO: 2)) which is part of the 5' end sequence of exon 3 of IGF-1. The PCR products were cloned into the pCR™ vector (Invitrogen) for DNA sequencing. Fragments were later sequenced by the dideoxy chain-termination method [2]. A total of 98% of the DNA sequence was obtained on both strands.

RESULTS

Northern Blotting. The results of Northern blot analysis performed with RNA extracted from normal and stretched extensor digitorum longus (EDL) are depicted in FIG. 1. The 280 bp IGF-1 antisense probe containing sequences derived from exon 3, and 4 of the IGF-1 gene hybridized with the two prominent IGF-1 mRNA species, 1.2 kb and 7.5 kb long. The expression of both types of mRNA species was greater in stretched muscle, although in some muscles the control muscle expressed more 7.5 kb mRNA than the stretched muscle.

Localization of IGF-1 mRNA in normal and stretched, muscle: Expression of IGF-1 mRNA within normal and stretched muscle studied by in situ hybridization using antisense and sense RNA probe is shown in FIG. 2. The in situ hybridization data demonstrates that the mRNA of IGF-1 is produced in response to stretch at the muscle fibre level as result of mechanical stimulation. This work showed that IGF-1 gene expression is not confined to the satellite cells but is up-regulated in the muscle fibres themselves. In transverse sections the IGF-1 message was localized to large muscle fiber but tended to be expressed strongly in the small fibres which represent the tapered ends of fibres terminating in the muscle belly [22]. In a few muscles some evidence of degeneration and regeneration was noted with high IGF-1 mRNA levels. These regions were superficial and indicated that in these cases the plaster cast was too tight. The in situ hybridization study however showed that with the use of the simple stretch model the upregulation of IGF-1 occurred in apparently undamaged fibres.

Molecular cloning of muscle IGF-1 cDNAs: This study was designed to investigate if different isoforms of IGF-1 are expressed in muscle when it is subjected to mechanical activity. Ten clones covering the E domain (exons three to six) were isolated and sequenced from stretched and from contralateral control muscle. Two classes of cDNA clone were obtained using RNA isolated from stretched muscle. Among these clones, 30% contain the sequences coding for IGF-1Ea and 70% for IGF-1Eb. However, even after repeated attempts, only IGF-1Ea type clones could be isolated from unstretched rabbit muscle. The cloned cDNA sequence starts from exon 3 which codes for mature IGF-1. The sequences of the two classes of IGF-1 cDNA isolated from total RNA of the stretched EDL muscle are shown in FIG. 3. The sequence may be divided into three sections. A region which encodes mature IGF-1 (peptides B, C, A and D), an extension E peptide which in IGF-1Eb has a 52 base insert which is lacking in IGF-1Ea, and a common 3' untranslated region. In terms of the carboxyl-terminal extension (E) peptide, the rabbit amino acid sequence is identical to the human sequence up to residue E 16. At the first base of the codon for residue E 17, the amino acid sequences of the two cDNA clones diverge due to the 52-bp insert in the IGF-1Eb clone. The insert changes the derived amino acid sequence as well as the reading frame, resulting in two possible carboxyl-terminal E peptide sequences and the presence of two-different UAG stop codons in end variants.

Comparing the 52-bp insert from rabbit muscle with the 52-bp insert in the IGF-1Eb expressed in rat liver in very low amounts [14] and IGF-1Ec which has recently been detected in human liver [15], the positions where the insert occurs is the same. The rabbit cDNA sequence shows 77% homology with rat IGF-1Eb, with 12 of the 17 expected amino acid sequences being identical and 94% with human IGF-1Ec, with 13 of 16 expected amino acid sequence being identical (FIG. 4).

DISCUSSION

Experimental models of muscle regeneration indicated that IGF-1 may act as a trophic factor in muscle regeneration [23] and it is expressed in proliferating myoblasts and satellite cells [24]. In this study we have analysed IGF-1 mRNA in skeletal muscle induced to undergo rapid longitudinal growth. This model was chosen as there is very little injury to the muscle fibres. The results presented here agree with published work [25–27] that IGF-1 mRNA is expressed in muscle tissues. However, they also show that the IGF-1 gene is expressed in the muscle fibres themselves and not solely in satellite and connective tissue cells. The expression of the IGF-1 transcripts was not uniform and it is usually the smaller fibres that show high levels of IGF-1 mRNA. A study of transverse and longitudinal sections showed that the small fibre which expressed IGF-1 mRNA also express the neonatal myosin heavy chain (MyHC). It has also been shown that small diameter fibres containing neonatal MyHC are the tapered ends of the larger fibres terminating within the belly of the muscle [22]. Longitudinal growth of skeletal muscle is facilitated by the addition of new sarcomeres to the ends of the existing myofibrils [28, 29] and the initial stage involves the laying down of neonatal myosin [22]. These data support the hypothesis that the ends of normal adult fibres are the region for longitudinal growth and that IGF-1 is involved in this process.

The estimation of the expression of the IGF-1 mRNA by Northern blotting suggests that both the 7.5 kb and 1.2 kb IGF-1 mRNA species are specifically induced by mechanical stimulation, but their increase seems to be independent of each other. The 1.2 kb mRNA was increased in all stretched muscle which was not always the case for the 7.5 kb mRNA At this stage we do not know which is transcript for the IGF-1 Eb. Further work is needed to characterise these mRNA and to determine what coding signal sequence and other elements they include.

The isolation of two classes of cDNA clones (IGF-1Ea and IGF-1Eb) from stretched muscle indicates that both forms of IGF-I mRNA are present in the stretched muscle. The IGF-1Ea and IGF-1Eb cDNA 3' sequences differ by the presence of a 52-bp insert which in the latter alters the derived carboxyl-terminal amino acid sequence. Three mechanisms may account for the 52 bp insert. Firstly, the insert could be generated by an alternate splice donor site 52-bp into the 5'-end of an intron present at this position in the IGF-1 genomic sequence. Alternatively, it may be generated by the use of an alternate splice acceptor site 52 bp from the 3'-end of the pertinent intron. Finally, the 52-bp insert could arise from a completely separate exon [10].

A comparison of the sequence of the rabbit IGF-1Eb with sequences of the rat IGF-1Eb [10] and human IGF-1Ec [15] showed that the IGF-1Eb which is markedly up-regulated in stretched muscle is apparently the rabbit counterpart to the rat IGF-1Eb and the human IGF-1Ec. Our results showed rabbit IGF-1Eb (the equivalent of human IGF-1Ec) was only detectable in stretched muscle. The fact that this is inducible isoform is consistent with the results of Chew et al [15] who demonstrated that after stimulation with physiological levels of GH, human IGF-1Ec transcript was increased in human hepatoma HepG2 cells (a hepatoma line), relative to human IGF-1Ea. The site for IGF-1 binding proteins (BP) is believed to be in the B domain [30]. Also C and D-domains, are thought to be "active regions" [31]. However, the physiological role of the alternative E peptide generated from IGF-1Ea and IGF-1Eb mRNA remains unknown [14]. It has been suggested that it could affect the interaction of IGF-1 with its receptor or its binding proteins. It has been also suggested that the E-peptides themselves may also have distinct biological roles after being cleaved from the pro-hormone [14]. Recently, part of the E-peptide has been shown to contain an amidated growth-promoting peptide with specific binding sites in human tissues [32]. According to our findings, the Eb-peptide appears to be induced only in the stretched muscle. This suggests the Eb-peptide may play a role in local growth control as exemplified by skeletal muscle fibre increasing in length and mass in response to mechanical stretch. The Eb peptide may be involved in the externalization of IGF-1 and also the binding of IGF-1 to muscle receptors.

There is evidence which suggests that the Ea peptide may be glycosylated in vivo. Bach et al [33] found that the Ea peptide can be glycosylated following in vitro translation in the presence of microsome. No putative glycosylation sites were noted from the muscle IGF-1 Eb sequence data. Possible functions for the differences in glycosylation of Ea and Eb include the reduction of the half life of IGF-1 1Eb, differential localization of the two forms and differential affinities for binding proteins. Therefore, the stretched muscle type IGF-1Eb maybe much smaller but with a shorter half-life than the isoforms produced by normal muscle and the liver.

Devol et al [34] reported that IGF-1 mRNA in skeletal muscle is independent of GH and other pituitary hormones and demonstrated a link between local stimulation of skeletal muscle growth and IGF-1 gene expression. The Eb expressed only in stretched muscle indicates that the expression of IGF-1Eb mRNA might be switched on by mechanical stimulation, which is known to induce rapid muscle growth [16]. The Eb peptide may then be a specific factor distinguishing mechanical stimulation and associated mechanisms of muscle growth.

It is apparent from our study that the different E peptides may play different roles in IGF-1 activity. Further studies are required to elucidate whether the E peptide of these alternative IGF-1 mRNA interact differently with the IGF-1 receptor or with IGF-1 binding proteins, or whether the alternative E peptide alone enables the growth factor to act in an autocrine fashion.

REFERENCES

[1] de Pagter-Holthuizen, P., van Schain, F. M. A, Verduijin G. M., van Ommen, G. J. B., Bouma, B. N., Jansen, M., and Sussenbach, J. S. (1986) FEBS Lett. 195, 179–184.

[2] Rotwein, P., Pollock, K M., Didier, D. K, Krivi G. G. (1986) J. Biol. Chem 261,4828–4832.

[3] Shimatsu, A. and Rotwein, P. (1987) J. Biol/Chem 262, 7894–7900.

[4] Tobin, G., Yee, D., Brunner, N. and Rotwein, P. (1990) Mol. Endocrinol. 4 (12), 1914–1920.

[5] Jansen, E., Steenbergh, P. H., LeRoith, D., Roberts, C T Jr. and Sussenbach J. S. (1991) Mol. Cell. Endocrinol. 78 (1–2), 115–125.

[6] Adamo M. L., Ben-Hur, H., Roberts, C T Jr. and LeRoith, D. (1991) Mol. Endocrinol. 5(11), 1677–1686.

[7] Dickson, M C., Saunders J C. and Gilmour R S. (I 99 i) J. Mol. Endocrinol. 6 (1), 17–31.

[8] Weller, P. A., Dickson, M. C., Huskisson, N. S., Dauncey, M. J., Buttery P. J. and Gilmour, R. S. (1993) J. Mol. Endocrinol. 11, 201–211.

[9] Rinderknecht E. and Humbel R. E. (1987) J. Biol. Chem 253, 2769–2776.

[10] Roberts, C T Jr., Lasky, S. T., Lowe, W L Jr. Seaman, W. T. and LeRoith, D. (1987) Mol. Endocrinol. 1, 243–248.

[11] Jansen M. van Schaik F. M. A, Ricker A. T.,Bullock B., Woods, D. E.,Gabbay K. R., Nussbaum, A. L., Sussenbach, J. S. and Van den Brande, J. L. (1983) Nature 306, 609–611.

[12] Bell, G. I., Merryweather, J. P., Sanchez-Pescador, R., Stempien, M. M., Priestley, L., Scott, J. and Rall, L B. (1984) Nature 310, 775–777.

[13] Powell, D. R., Lee, P. D., Chang D. Liu, F. and Hintz, R. L. (1987) J. Clin. Endocrinol. Metab. 65, 868–875.

[14] Lowe, W L Jr., Lasky, S. R., LeRoith, D. and Roberts C T Jr. (1988) Mol. Endocrinol. 2, 528–535.

[15] Chew, S. L., Lavender P., Clark A. J. L. and Ross R. J. M. (1995) Endocrinology 136, 1939–1944.

[16] Goldspink, G., Scutt, A., Loughna P. T., Wells, D. J., Jaenicke, T. and Gerlach, G. F. (1992) Am. J. Physiol. 263 (3 Pt 2) R 356–363.

[17] Tabary, J. C., Tabary, C., Tardieu C. Tardieu G. and Goldspink G. (1972) J. Physiol. 224(1), 231–244.

[18] Golspink, D. F. Morton, A. J., Loughna, P. and Goldspink G. (1986) Pflugers Archiv-European Journal of Physiology 407 (3), 333–340.

[19] Goldspink, D. F., Cox, V. M., Smith, S. K, Eaves, L. A., Osbaldeston, N. J., Lee, D. M. and Mantle, D. (1995) Am. J. Physiol. 268, E288-E297.

[20] Chiomczynski, P. and Sacchi, N, (1987) Analyt. Blochem. 162, 156–159.

[21] Sanger, F., Nicklen, S. and Coulson, A. R. (1977) Proc. Natl. Acad. Sci. USA 74, 54635467.

[22] Benjamin, W. C., Donna, M. W., Stacey, D. L., Jacalyn, D. A. and Everett, B. (1995) The Anatomical Record 242, 462–470.

[23] Jennische, E., Skottner, A. and Hansson, H. A. (1987) Acta Physiol. Scand. 129, 9.

[24] Edwall, D., Schalling, M., Jennische, E. and Norstedt, G. (1989) Endocrinology 124, 820 825.

[25] Beck, F., Samani, N. J., Penschow, J. D., Thorley, B., Tregear, G. W. and Coghlan, J. P. (1987) Development 101, 175–184.

[26] Han, V. K M., D'Erocole, A. J. and Lund, P. K (1987) Science 236,193–197.

[27] Caroni, P. and Schneider C. (1994) J. Neurosci. 14, 3378–3388.

[28] Williams, P. E. and Goldspink, G. (1971) J. Cell Sci 9, 751–767.

[29] Williams, P. E. and Goldspink, G. (1973) J. Anat. 116,45–46.

[30] DeVroede, M. A., Rechler, M. M., Nissley, S. P., Josni, S., Burke, G. T. and Katsoyannis, P. G. (1985) Proc. Natl. Acad. Sci. USA 82, 3010–3014.

[31] Pietrkowski, Z., Wernicke, D., Porcu, P., Jameson, B. A. and Baserga, R. (1992) Cancer Res. 52, 6447–6451.

[32] Siegfhed, L. M., Kasprzyk, P. G., Treston, A. M., Mulshine J. L., Quinn, K A and Cuttitta F. (1992) Proc. Natl. Acad. Sci. USA 89 (17), 8107–8111.

[33] Bach M. A., Roberts C T Jr., Smith E. P. and LeRoith, D. (1990) Mol Endocrinol. 4(6), 899–904.

[34] Devol, D. L., Rotwein, P., Sadow, J. L., Novakofski, J. and Bechtel, P. J. (1990) Am. J. Physiol. 259, E89–E95.

What is claimed is:

1. A pharmaceutical composition comprising an IGF-I polypeptide, said polypeptide comprising peptides encoded by IGF-I exons 4, 5 and 6 when transcribed in the reading frame of the mechanical-stimulation-specific, stretch-inducible IGF-I isoform present in stretched EDL muscle and said polypeptide having the ability to induce growth of muscle tissue.

2. A method for the treatment of muscular disorders of the human or animal body which comprises administering to a patient in need of such treatment an effective amount of an IGF-I polypeptide, said polypeptide comprising peptides encoded by IGF-I exons 4, 5 and 6 when transcribed in the reading frame of the mechanical-stimulation-specific, stretch-inducible IGF-I isoform present in stretched EDL muscle and said polypeptide having the ability to induce growth of muscle tissue.

3. A method for the treatment of muscular disorders of the human body which comprises administering to a human patient in need of such treatment an effective amount of an IGF-I polypeptide said polypeptide comprising peptides encoded by IGF-I exons 4, 5 and 6 when transcribed in the reading frame of the mechanical-stimulation-specific, stretch-inducible IGF-I isoform present in stretched EDL muscle and said polypeptide having the ability to induce growth of muscle tissue.

4. The method of claim 3 wherein the polypeptide is a human polypeptide.

5. A method for the treatment of muscular disorders of the animal body which comprises administering to an animal patient in need of such treatment an effective amount of an IGF-I polypeptide, said polypeptide comprising peptides encoded by IGF-I exons 4, 5 and 6 when transcribed in the reading frame of the mechanical-stimulation-specific, stretch-inducible IGF-I isoform present in stretched EDL muscle and said polypeptide having the ability to induce growth of muscle tissue.

6. The method of claim 5 wherein the polypeptide is an animal polypeptide.

7. A method for the treatment of muscular disorders according to claim 2 wherein the muscular disorder is muscular dystrophy.

8. A method for the treatment of muscular disorders according to claim 3 wherein the muscular disorder is muscular dystrophy.

9. A method for the treatment of muscular disorders according to claim 4 wherein the muscular disorder is muscular dystrophy.

10. A method for the treatment of muscular disorders according to claim 5 wherein the muscular disorder is muscular dystrophy.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 1:

TTGGGCATGT CAGTGTGG                                          18

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:    2:

GCTTGCTCAC CTTTACCAGC                                      20

(2) INFORMATION FOR SEQ ID NO: 3:

(i) SEQUENCE CHARACTERISTICS:
        (A) LENGTH: 553 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION:1..363

(xi) SEQUENCE DESCRIPTION: SEQ ID NO: 3:

```
TTG CTC ACC TTT ACC AGC TCG GCC ACA GCC GGA CCG GAG ACG CTC TGC        48
Leu Leu Thr Phe Thr Ser Ser Ala Thr Ala Gly Pro Glu Thr Leu Cys
 1               5                  10                  15

GGT GCT GAG CTG GTG GAT GCT CTT CAG TTC GTG TGT GGA GAC AGG GGC        96
Gly Ala Glu Leu Val Asp Ala Leu Gln Phe Val Cys Gly Asp Arg Gly
             20                  25                  30

TTT TAT TTC AAC AAG CCC ACA GGA TAC GGC TCC AGC AGT CGG AGG GCA       144
Phe Tyr Phe Asn Lys Pro Thr Gly Tyr Gly Ser Ser Ser Arg Arg Ala
         35                  40                  45

CCT CAG ACA GGC ATC GTG GAT GAG TGC TGC TTC CGG AGC TGT GAT CTG       192
Pro Gln Thr Gly Ile Val Asp Glu Cys Cys Phe Arg Ser Cys Asp Leu
     50                  55                  60

AGG AGG CTG GAG ATG TAC TGT GCA CCC CTC AAG CCG GCA AAG GCA GCC       240
Arg Arg Leu Glu Met Tyr Cys Ala Pro Leu Lys Pro Ala Lys Ala Ala
 65                  70                  75                  80

CGC TCC GTC CGT GCC CAG CGC CAC ACC GAC ATG CCC AAG ACT CAG AAG       288
Arg Ser Val Arg Ala Gln Arg His Thr Asp Met Pro Lys Thr Gln Lys
                 85                  90                  95

TAT CAG CCT CCA TCT ACC AAC AAG AAA ATG AAG TCT CAG AGG AGA AGG       336
Tyr Gln Pro Pro Ser Thr Asn Lys Lys Met Lys Ser Gln Arg Arg Arg
            100                 105                 110

AAA GGA AGT ACA TTT GAA GAA CAC AAG TAGAGGGAGT GCAGGAAACA             383
Lys Gly Ser Thr Phe Glu Glu His Lys
        115                 120
```

```
AGAACTACAG GATGTAGGAA GACCCTTCTG AGGAGTGAAG AAGGACAGGC CACCGCAGG      443

CCCTTTGCTC TGCACAGTTA CCTGTAAACA TTGGAATACC GGCCAAAAAA TAAGTTTGA      503

CACATTTCAA AGATGGCATT TCCCCCAATG AAATACACAA GTAAACATTC                553
```

(2) INFORMATION FOR SEQ ID NO: 4:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO: 4:

```
Leu Leu Thr Phe Thr Ser Ser Ala Thr Ala Gly Pro Glu Thr Leu Cys
 1               5                  10                  15

Gly Ala Glu Leu Val Asp Ala Leu Gln Phe Val Cys Gly Asp Arg Gly
            20                  25                  30

Phe Tyr Phe Asn Lys Pro Thr Gly Tyr Gly Ser Ser Arg Arg Ala
        35                  40                  45

Pro Gln Thr Gly Ile Val Asp Glu Cys Cys Phe Arg Ser Cys Asp Leu
    50                  55                  60

Arg Arg Leu Glu Met Tyr Cys Ala Pro Leu Lys Pro Ala Lys Ala Ala
65                  70                  75                  80

Arg Ser Val Arg Ala Gln Arg His Thr Asp Met Pro Lys Thr Gln Lys
                85                  90                  95

Tyr Gln Pro Pro Ser Thr Asn Lys Lys Met Lys Ser Gln Arg Arg Arg
            100                 105                 110

Lys Gly Ser Thr Phe Glu Glu His Lys
            115                 120
```

(2) INFORMATION FOR SEQ ID NO: 5:

(i) SEQUENCE CHARACTERISTICS:
        (A) LENGTH: 553 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION:341..397

(xi) SEQUENCE DESCRIPTION: SEQ ID NO: 5:

```
TTGCTCACCT TTACCAGCTC GGCCACAGCC GGACCGGAGA CGCTCTGCGG TGCTGAGCTG      60

GTGGATGCTC TTCAGTTCGT GTGTGGAGAC AGGGGCTTTT ATTTCAACAA GCCCACAGG     120

TACGGCTCCA GCAGTCGGAG GGCACCTCAG ACAGGCATCG TGGATGAGTG CTGCTTCCG     180

AGCTGTGATC TGAGGAGGCT GGAGATGTAC TGTGCACCCC TCAAGCCGGC AAAGGCAGC     240

CGCTCCGTCC GTGCCCAGCG CCACACCGAC ATGCCCAAGA CTCAGAAGTA TCAGCCTCC     300

TCTACCAACA AGAAAATGAA GTCTCAGAGG AGAAGGAAAG GAA GTA CAT TTG AAG      355
                                             Glu Val His Leu Lys
                                                              125

AAC ACA AGT AGA GGG AGT GCA GGA AAC AAG AAC TAC AGG ATG              397
Asn Thr Ser Arg Gly Ser Ala Gly Asn Lys Asn Tyr Arg Met
            130                 135                 140

TAGGAAGACC CTTCTGAGGA GTGAAGAAGG ACAGGCCACC GCAGGACCCT TTGCTCTGC     457
```

```
CAGTTACCTG TAAACATTGG AATACCGGCC AAAAAATAAG TTTGATCACA TTTCAAAGA      517

GGCATTTCCC CCAATGAAAT ACACAAGTAA ACATTC                              553
```

(2) INFORMATION FOR SEQ ID NO: 6:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 6:

```
Glu Val His Leu Lys Asn Thr Ser Arg Gly Ser Ala Gly Asn Lys Asn
 1               5                  10                  15

Tyr Arg Met
```

(2) INFORMATION FOR SEQ ID NO: 7:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO: 7:

```
Tyr Gln Pro Pro Ser Thr Asn Lys Lys Met Lys Ser Gln Arg Arg Ar
 1               5                  10                  15
```

(2) INFORMATION FOR SEQ ID NO: 8:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO: 8:

```
Tyr Gln Pro Pro Ser Thr Asn Lys Asn Thr Lys Ser Gln Arg Arg Ly
 1               5                  10                  15
```

(2) INFORMATION FOR SEQ ID NO: 9:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO: 9:

```
Ser Gln Pro Leu Ser Thr His Lys Lys Arg Lys Leu Gln Arg Arg Ar
 1               5                  10                  15
```

(2) INFORMATION FOR SEQ ID NO: 10:

(i) SEQUENCE CHARACTERISTICS:
        (A) LENGTH: 777 base pairs
        (B) TYPE: nucleic acid
        (C) STRANDEDNESS: both
        (D) TOPOLOGY: linear (ii) MOLECULE TYPE: cDNA (ix) FEATURE:

(A) NAME/KEY: CDS
        (B) LOCATION:26..493

(xi) SEQUENCE DESCRIPTION: SEQ ID NO: 10:

| | | | | | | | | | | | | | | | |
|---|---|---|---|---|---|---|---|---|---|---|---|---|---|---|---|
| CTGCAGGGGG | GGGGGGGGGG | GGGCT | TCA | GAA | GCA | ATG | GGA | AAA | ATC | AGC | AGT | | | | 52 |
| | | | Ser | Glu | Ala | Met | Gly | Lys | Ile | Ser | Ser | | | | |
| | | | 20 | | | | | 25 | | | | | | | |

```
CTT CCA ACC CAA TTA TTT AAG TGC TGC TTT TGT GAT TTC TTG AAG GTG          100
Leu Pro Thr Gln Leu Phe Lys Cys Cys Phe Cys Asp Phe Leu Lys Val
    30                  35                  40

AAG ATG CAC ACC ATG TCC TCC TCG CAT CTC TTC TAC CTG GCG CTG TGC          148
Lys Met His Thr Met Ser Ser Ser His Leu Phe Tyr Leu Ala Leu Cys
45                  50                  55                  60

CTG CTC ACC TCC ACC AGC TCT GCC ACG GCT GGA CCG GAG ACG CTC TGC          196
Leu Leu Thr Ser Thr Ser Ser Ala Thr Ala Gly Pro Glu Thr Leu Cys
                65                  70                  75

GGG GCT GAG CTG GTG GAT GCT CTT CAG TTC GTG TGT GGA GAC AGG GGC          244
Gly Ala Glu Leu Val Asp Ala Leu Gln Phe Val Cys Gly Asp Arg Gly
            80                  85                  90

TTT TAT TTC AAC AAG CCC ACA GGG TAT GGC TCC AGC AGT CGG AGG GCG          292
Phe Tyr Phe Asn Lys Pro Thr Gly Tyr Gly Ser Ser Ser Arg Arg Ala
        95                  100                 105

CCT CAG ACA GGT ATC GTG GAT GAG TGC TGC TTC CGG AGC TGT GAT CTA          340
Pro Gln Thr Gly Ile Val Asp Glu Cys Cys Phe Arg Ser Cys Asp Leu
    110                 115                 120

AGG AGG CTG GAG ATG TAT TGC GCA CCC CTC AAG CCT GCC AAG TCA GCT          388
Arg Arg Leu Glu Met Tyr Cys Ala Pro Leu Lys Pro Ala Lys Ser Ala
125                 130                 135                 140

CGC TCT GTC CGT GCC CAG CGC CAC ACC GAC ATG CCC AAG ACC CAG AAG          436
Arg Ser Val Arg Ala Gln Arg His Thr Asp Met Pro Lys Thr Gln Lys
                145                 150                 155

GAA GTA CAT TTG AAG AAC GCA AGT AGA GGG AGT GCA GGA AAC AAG AAC          484
Glu Val His Leu Lys Asn Ala Ser Arg Gly Ser Ala Gly Asn Lys Asn
            160                 165                 170

TAC AGG ATG TAGGAAGACC CTCCTGAGGA GTGAAGAGTG ACATGCCACC                  533
Tyr Arg Met
        175

GCAGGATCCT TTGCTCTGCA CGAGTTACCT GTTAAACTTT GGAACACCTA CCAAAAAAT         593

AGTTTGATAA CATTTAAAAG ATGGGCGTTT CCCCCAATGA AATACACAAG TAAACATTC         653

AACATTGTCT TTAGGAGTGA TTTGCACCTT GCAAAAATGG TCCTGGAGTT GGTAGATTG         713

TGTTGATCTT TTATCAATAA TGTTCTATAG AAAAGAAAAA AAACCCCCC CCCCCCCCC          773

GCAG                                                                     777
```

(2) INFORMATION FOR SEQ ID NO: 11:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO: 11:

```
Ser Glu Ala Met Gly Lys Ile Ser Ser Leu Pro Thr Gln Leu Phe Lys
1               5                   10                  15

Cys Cys Phe Cys Asp Phe Leu Lys Val Lys Met His Thr Met Ser Ser
            20                  25                  30

Ser His Leu Phe Tyr Leu Ala Leu Cys Leu Leu Thr Ser Thr Ser Ser
        35                  40                  45
```

```
Ala Thr Ala Gly Pro Glu Thr Leu Cys Gly Ala Glu Leu Val Asp Ala
    50                  55                  60

Leu Gln Phe Val Cys Gly Asp Arg Gly Phe Tyr Phe Asn Lys Pro Thr
65                  70                  75                  80

Gly Tyr Gly Ser Ser Ser Arg Arg Ala Pro Gln Thr Gly Ile Val Asp
                85                  90                  95

Glu Cys Cys Phe Arg Ser Cys Asp Leu Arg Arg Leu Glu Met Tyr Cys
                100                 105                 110

Ala Pro Leu Lys Pro Ala Lys Ser Ala Arg Ser Val Arg Ala Gln Arg
            115                 120                 125

His Thr Asp Met Pro Lys Thr Gln Lys Glu Val His Leu Lys Asn Ala
    130                 135                 140

Ser Arg Gly Ser Ala Gly Asn Lys Asn Tyr Arg Met
145                 150                 155
```